(12) United States Patent
Hsieh

(10) Patent No.: US 9,645,061 B2
(45) Date of Patent: May 9, 2017

(54) BOLT TENSION GAUGING APPARATUS

(71) Applicant: KABO TOOL COMPANY, Taichung (TW)

(72) Inventor: Chih-Ching Hsieh, Taichung (TW)

(73) Assignee: KABO TOOL COMPANY, Taichung (TW)

( * ) Notice: Subject to any disclaimer, the term of this patent is extended or adjusted under 35 U.S.C. 154(b) by 153 days.

(21) Appl. No.: 14/682,096

(22) Filed: Apr. 8, 2015

(65) Prior Publication Data

US 2015/0292996 A1 Oct. 15, 2015

(30) Foreign Application Priority Data

Apr. 10, 2014 (TW) .............................. 103206241 U

(51) Int. Cl.
| | |
|---|---|
| *F16B 31/02* | (2006.01) |
| *G01N 3/08* | (2006.01) |
| *G01L 5/24* | (2006.01) |
| *G01L 1/16* | (2006.01) |
| *G01L 5/16* | (2006.01) |
| *G01L 5/00* | (2006.01) |
| *G01L 1/22* | (2006.01) |

(52) U.S. Cl.
CPC .................. *G01N 3/08* (2013.01); *F16B 31/02* (2013.01); *G01L 5/24* (2013.01); *F16B 31/025* (2013.01); *G01L 1/16* (2013.01); *G01L 1/22* (2013.01); *G01L 5/0004* (2013.01); *G01L 5/161* (2013.01); *Y10S 411/916* (2013.01)

(58) Field of Classification Search
CPC .......... G01L 5/24; G01L 5/0004; G01L 5/161; G01L 1/16; G01L 1/22; F16B 31/02; F16B 31/025; Y10S 411/916

USPC ............ 73/761, 768, 862.629, 763, 862.632; 411/14, 372.5, 916; 116/DIG. 34

See application file for complete search history.

(56) References Cited

U.S. PATENT DOCUMENTS

| | | | | |
|---|---|---|---|---|
| 3,799,108 | A | * | 3/1974 | Mosow .................... F16B 31/02 116/212 |
| 4,127,788 | A | * | 11/1978 | Daugherty ............ B06B 1/0644 310/328 |
| 4,553,124 | A | * | 11/1985 | Malicki ................. F16B 31/025 338/2 |
| 4,630,490 | A | * | 12/1986 | Malicki ..................... G01L 1/22 338/5 |

(Continued)

*Primary Examiner* — Jonathan Dunlap
(74) *Attorney, Agent, or Firm* — CKC & Partners Co., Ltd.

(57) ABSTRACT

A bolt tension gauging apparatus is provided with a bolt assembly including a bolt having a top cavity on a head and a recess on a surface of a threaded shank, and a covering element fitted onto the recess; an electrical resonant transformer on a bottom of the covering member; and a force transducer and transmitter assembly in the recess and electrically connected to the transformer. An electrical resonant transformation device causes the transformer to harvest power from radio frequency electromagnetic waves if a distance between the transformation device and the transformer is sufficiently short. The force transducer and transmitter assembly gauges tension of the bolt and converts same into a signal. The signal is transmitted to a controller and display device for calculating a difference between a predetermined tension and the gauged tension. An alert is generated if the gauged tension is greater than the predetermined tension.

4 Claims, 4 Drawing Sheets

(56) References Cited

U.S. PATENT DOCUMENTS

| | | | | |
|---|---|---|---|---|
| 5,226,765 | A * | 7/1993 | Walton | F16B 31/025 116/212 |
| 5,388,463 | A * | 2/1995 | Scott | G01L 5/24 73/761 |
| 7,400,247 | B2 * | 7/2008 | Hopman | G06K 19/04 340/545.2 |
| 7,412,898 | B1 * | 8/2008 | Smith | G01L 5/24 73/761 |
| 7,412,899 | B2 * | 8/2008 | Mian | G07C 3/00 340/870.18 |
| 7,832,281 | B2 * | 11/2010 | Mian | G07C 3/00 340/870.18 |
| 8,024,980 | B2 * | 9/2011 | Arms | G01L 1/2225 73/761 |
| 8,433,160 | B2 * | 4/2013 | Shah | G01D 5/35303 385/12 |
| 8,448,520 | B1 * | 5/2013 | Baroudi | G01L 5/0038 73/761 |
| 8,540,468 | B2 * | 9/2013 | Mekid | F16B 31/02 411/13 |
| 8,596,134 | B2 * | 12/2013 | Mekid | F16B 31/02 73/760 |
| 8,635,916 | B1 * | 1/2014 | Loverich | G01L 5/0004 73/768 |
| 8,646,162 | B2 * | 2/2014 | Clarke | G01L 5/24 29/402.06 |
| 8,695,432 | B2 * | 4/2014 | Hsieh | F16B 31/025 411/383 |
| 8,793,081 | B1 * | 7/2014 | Loverich | G01L 5/0004 340/683 |
| 9,121,777 | B2 * | 9/2015 | Hsieh | G01L 5/00 |
| 9,249,820 | B2 * | 2/2016 | Groche | B21K 25/00 |
| 2007/0062299 | A1 * | 3/2007 | Mian | G07C 3/00 73/763 |
| 2008/0253858 | A1 * | 10/2008 | Hsieh | F16B 31/02 411/14 |
| 2009/0000387 | A1 * | 1/2009 | Mian | G07C 3/00 73/763 |
| 2009/0151466 | A1 * | 6/2009 | Wu | G01L 5/24 73/761 |
| 2009/0210173 | A1 * | 8/2009 | Arms | G01L 1/2225 702/42 |
| 2010/0329602 | A1 * | 12/2010 | Shah | G01D 5/35303 385/13 |
| 2012/0185002 | A1 * | 7/2012 | Hsieh | F16B 31/025 606/315 |
| 2013/0064622 | A1 * | 3/2013 | Mekid | F16B 31/02 411/13 |
| 2013/0068031 | A1 * | 3/2013 | Mekid | F16B 31/02 73/761 |
| 2013/0139604 | A1 * | 6/2013 | Baroudi | G01L 5/0038 73/761 |
| 2014/0190267 | A1 * | 7/2014 | Mekid | G01L 1/16 73/761 |
| 2014/0283617 | A1 * | 9/2014 | Hsieh | G01L 5/00 73/761 |
| 2015/0247520 | A1 * | 9/2015 | Hsieh | F16B 31/02 411/14 |
| 2015/0247521 | A1 * | 9/2015 | Hsieh | F16B 35/00 411/8 |

* cited by examiner

BOLT TENSION GAUGING APPARATUS

RELATED APPLICATIONS

The application claims priority to Taiwan Application Serial Number 103206241, filed Apr. 10, 2014, which is herein incorporated by reference.

BACKGROUND OF THE INVENTION

1. Field of the Invention

The invention relates to threaded fasteners and more particularly to an apparatus for gauging tension of a bolt.

2. Description of Related Art

Bolted joints are found in a wide range of machines. However, loosened bolts may compromise the safety and structural integrity of a joint. Insufficient pre-loading tension is a common cause of bolted joint failure. Given the fact that most machines use hundreds or more bolts in their construction, it is impractical to regularly, manually test the tension of each bolt.

There is a conventional device for measuring the tension in a bolt and is characterized in that a tamper indicating fastener has a cylindrical body with threads extending from one end along a portion of the body, and a tamper indicator having a transducer for converting physical properties of the body into electronic data; electronics for recording the electronic data; and means for communicating the recorded information to a remote location from the fastener.

While the conventional bolt tension measuring device is successful in its applications, continuous improvements of the art are always sought.

SUMMARY OF THE INVENTION

It is therefore one object of the invention to provide a bolt tension gauging apparatus comprising an electrical resonant transformation device; a controller and display device; and a bolt assembly comprising a bolt including a head having a cavity on a top, and a partially threaded shank having a recess on a peripheral surface, and a covering element configured to fit onto the recess; an electrical resonant transformer formed on a bottom of the covering member and configured to dispose in the cavity; and a force transducer and transmitter assembly disposed in the recess, the force transducer and transmitter assembly being electrically connected to the electrical resonant transformer; wherein the electrical resonant transformation device is configured to cause the electrical resonant transformer to harvest power from radio frequency electromagnetic waves transmitted from the electrical resonant transformation device if a distance between the electrical resonant transformation device and the electrical resonant transformer is no more than a predetermined distance; wherein the power is supplied from the electrical resonant transformer to the force transducer and transmitter assembly for activation; wherein the activated force transducer and transmitter assembly gauges tension of the bolt and convert the gauged tension into a signal representing the gauged tension; wherein the signal is transmitted to the controller and display device so that the controller and display device calculates a difference between a predetermined tension and the gauged tension; and wherein an alert is generated if the gauged tension is greater than the predetermined tension.

The above and other objects, features and advantages of the invention will become apparent from the following detailed description taken with the accompanying drawings.

DETAILED DESCRIPTION OF THE INVENTION

Figure 1:
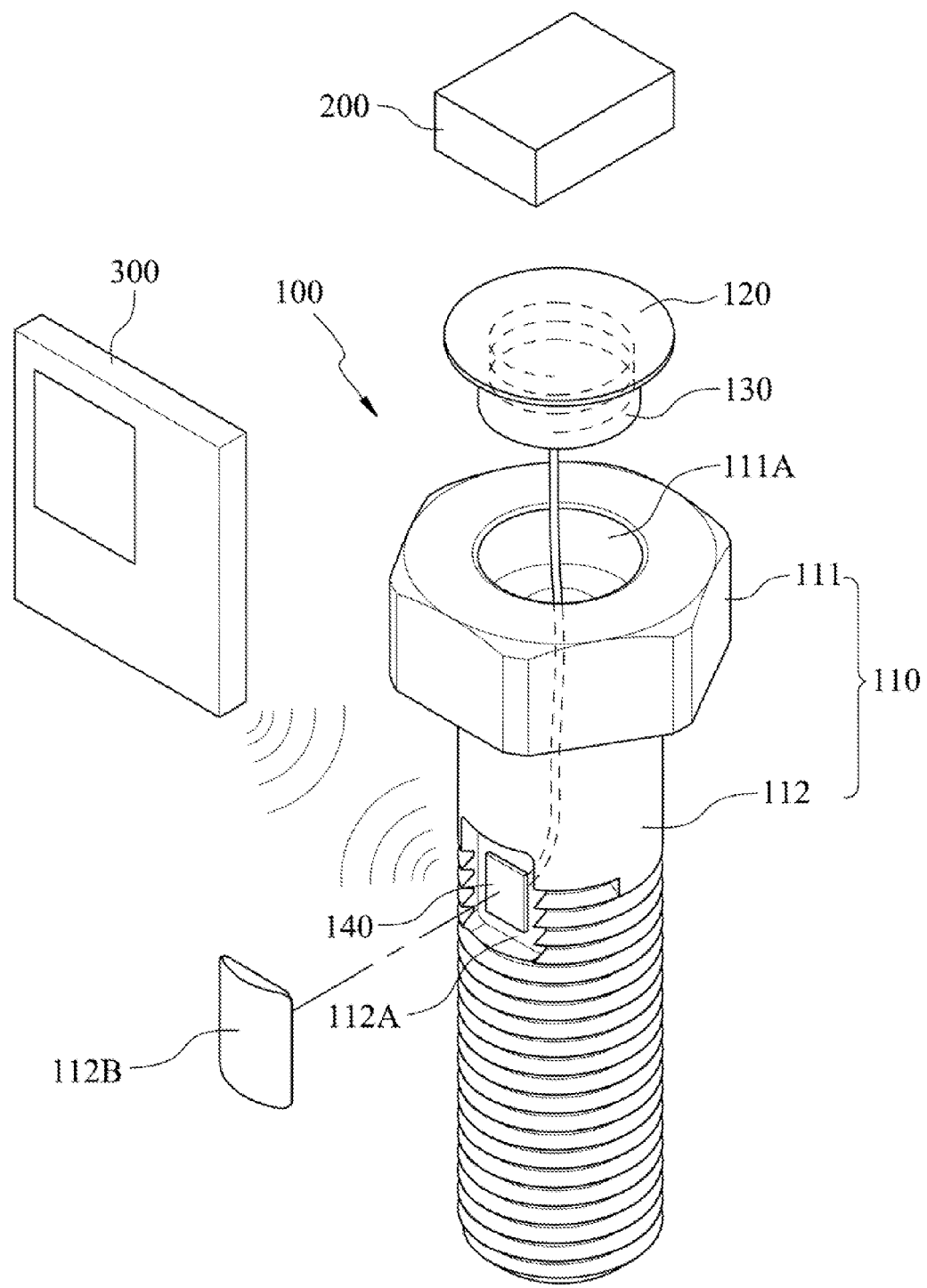
FIG. 1 is an exploded view of a bolt tension gauging apparatus according to a first preferred embodiment of the invention.

Referring to FIG. 1, a bolt tension gauging apparatus in accordance with the invention comprises the following components as discussed in detail below.

A bolt assembly 100 comprises a bolt 110 including a head 111 having a cavity 111A on a top, and a partially threaded shank 112 having a recess 112A on a peripheral surface, and a covering element 112B configured to fit onto the recess 112A; a disc shaped covering member 120; an electrical resonant transformer 130 disposed on a bottom of the covering member 120 and configured to fit into the cavity 111A so that the cavity 111A can be concealed by the covering member 120; and a force transducer and transmitter assembly 140 disposed in the recess 112A, the force transducer and transmitter assembly 140 being electrically connected to the electrical resonant transformer 130. As discussed above, the covering element 112B is fitted onto the recess 112A to conceal the force transducer and transmitter assembly 140.

An electrical resonant transformation device 200 can be brought to a position proximate to the electrical resonant transformer 130. The electrical resonant transformer 130 is activated to harvest power from radio frequency electromagnetic waves transmitted from the electrical resonant transformation device 200 if a distance between the electrical resonant transformation device 200 and the electrical resonant transformer 130 is no more than a predetermined distance. Further, the power is supplied from the electrical resonant transformer 130 to the force transducer and transmitter assembly 140 for activation. The force transducer and transmitter assembly 140 disposed in the shank 112 is urged against by a workpiece (not shown) in which the bolt 110 is fastened. The activated force transducer and transmitter assembly 140 can gauge tension of the bolt 110 and convert the tension into a signal. Finally, the signal is transmitted to a solar controller and display device 300 which in turn calculates a difference between a predetermined tension (stored in a memory (not shown) of the solar controller and display device 300) and the gauged tension. An alert is generated if the gauged tension is greater than the predetermined tension. The alert can be in the form of a visual display on a screen 310 of the solar controller and display device 300 or a buzzing sound made by the solar controller and display device 300.

Preferably, the wireless connection of the force transducer and transmitter assembly 140 and the solar controller and display device 300 is implemented by Bluetooth or near field communication (NFC).

Preferably, the electrical resonant transformation device 200 is a continuous wave oscillator and the electrical resonant transformer 130 is Tesla coil receiver configured to receive the nonradiating electromagnetic field energy produced by the electrical resonant transformation device 200.

The force transducer and transmitter assembly 140 is implemented by transistor such as metal-oxide-semiconductor field-effect transistor (MOSFET).

Figure 2:
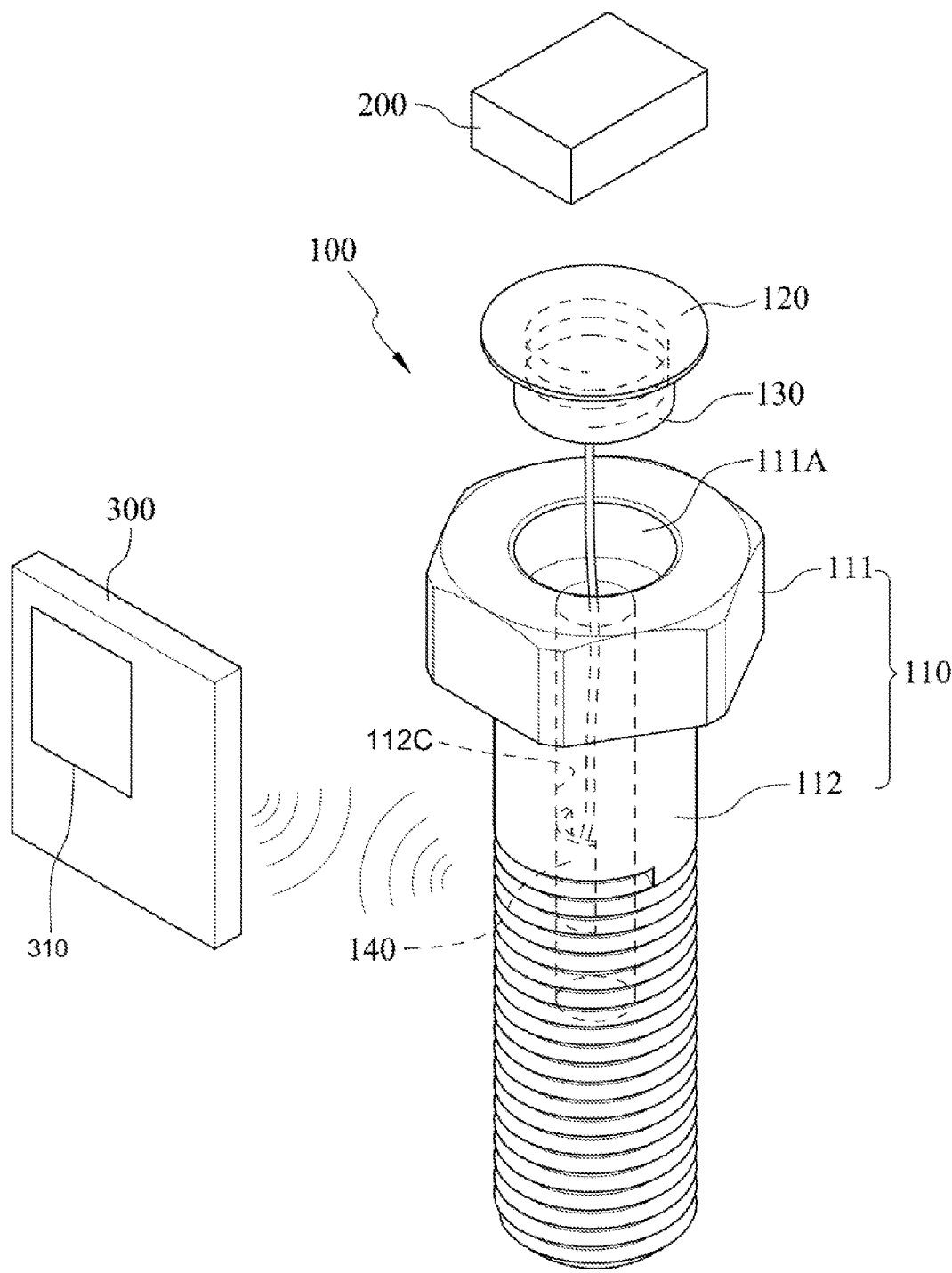
FIG. 2 is an exploded view of a bolt tension gauging apparatus according to a second preferred embodiment of the invention.

Referring to FIG. 2, a bolt tension gauging apparatus in accordance with a second preferred embodiment of the invention is shown. The characteristics of the second preferred embodiment are substantially the same as that of the first preferred embodiment except the following:

Both the covering element and the recess are eliminated. An hole 112C is formed in the shank 112 and has a top communicating with the cavity 111A. The force transducer and transmitter assembly 140 is provided on a surface of the hole 112C.

Figure 3:
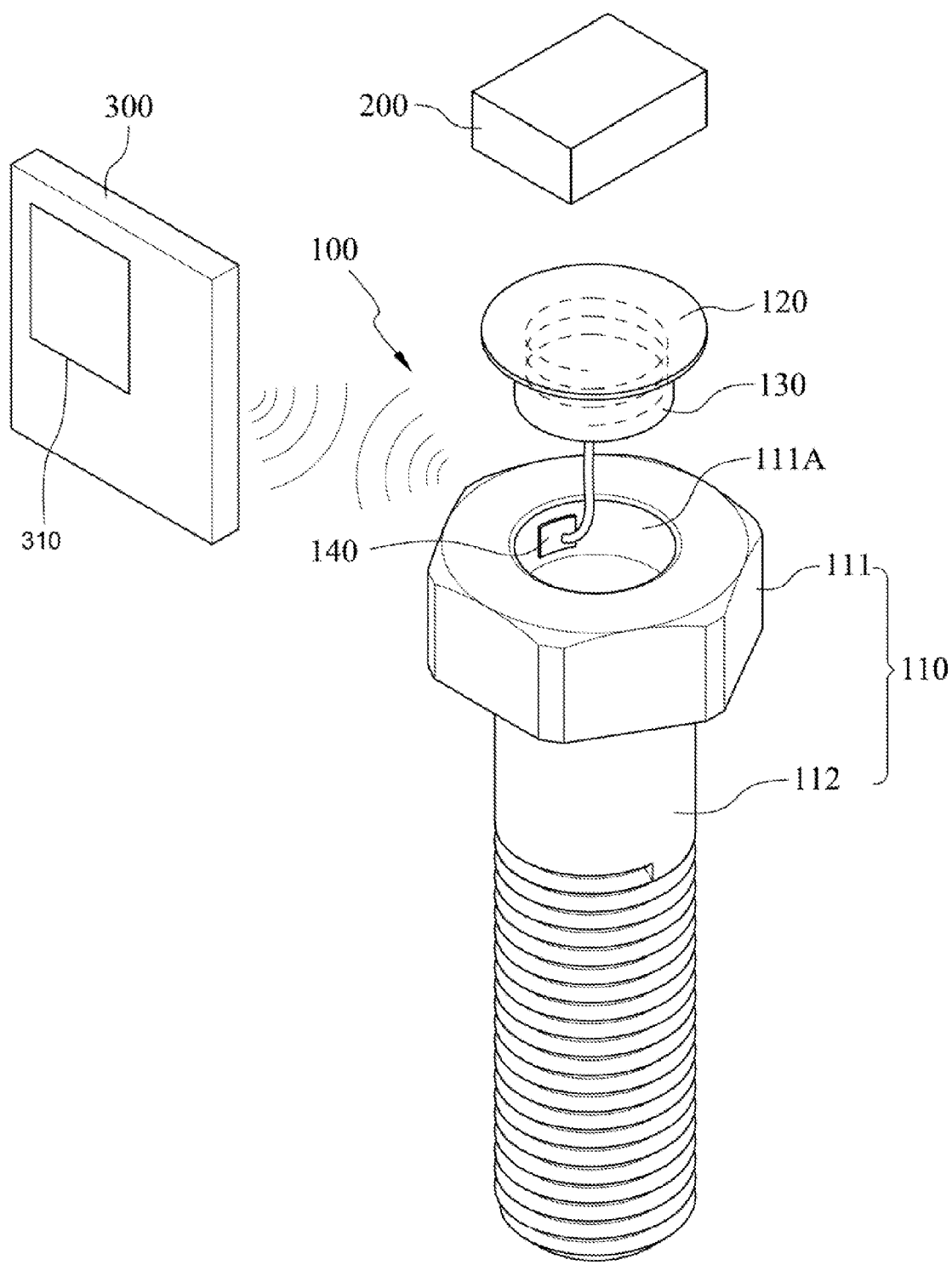
FIG. 3 is an exploded view of a bolt tension gauging apparatus according to a third preferred embodiment of the invention.

Referring to FIG. 3, a bolt tension gauging apparatus in accordance with a third preferred embodiment of the invention is shown. The characteristics of the third preferred embodiment are substantially the same as that of the first preferred embodiment except the following:

Both the covering element and the recess are eliminated. The force transducer and transmitter assembly 140 is provided on a peripheral surface of the cavity 111A.

Figure 4:
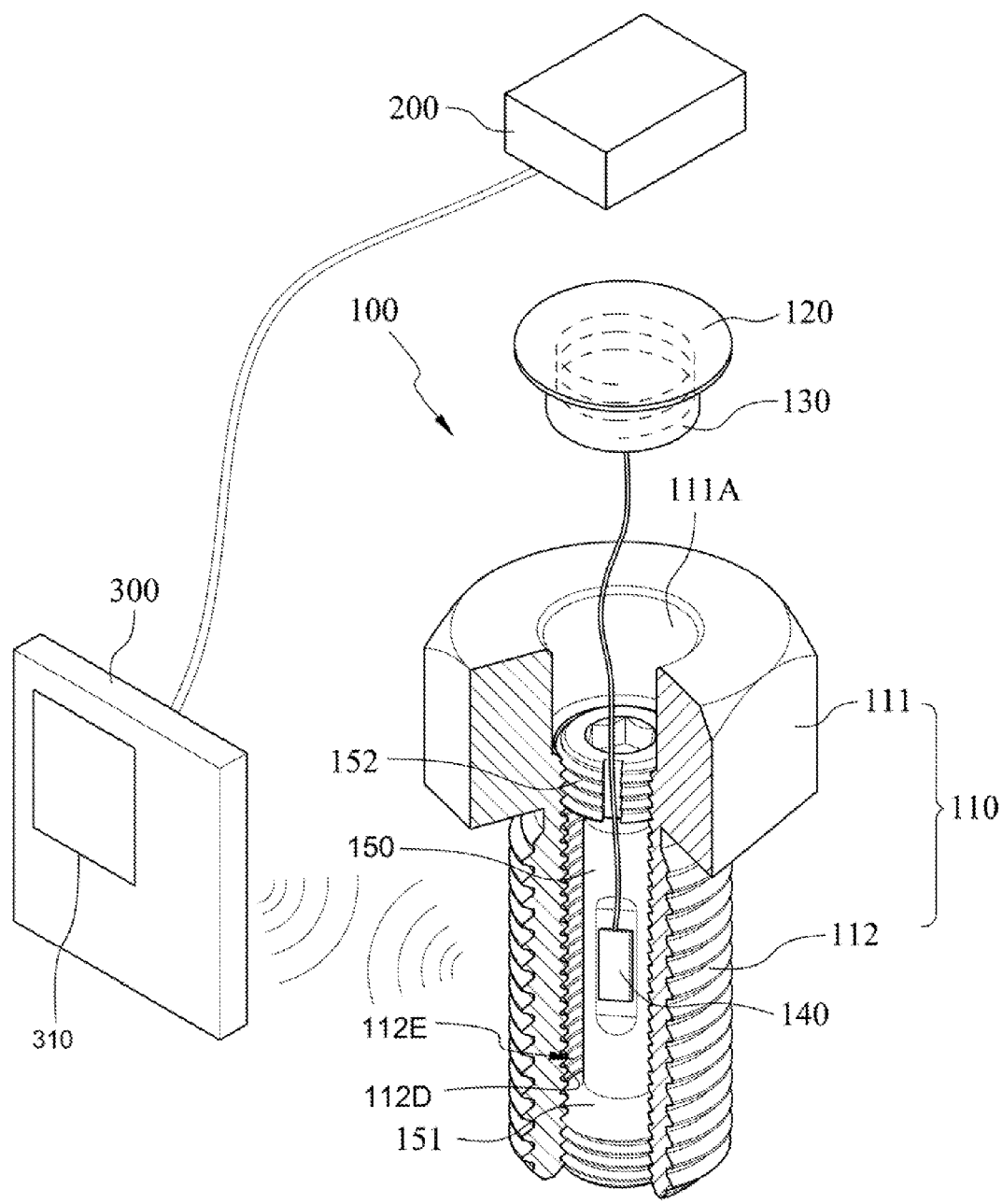
FIG. 4 is an exploded view of a bolt tension gauging apparatus according to a fourth preferred embodiment of the invention.

Referring to FIG. 4, a bolt tension gauging apparatus in accordance with a fourth preferred embodiment of the invention is shown. The characteristics of the fourth preferred embodiment are substantially the same as that of the first preferred embodiment except the following:

Both the covering element and the recess are eliminated. An axial channel 112D is formed in the shank 12. The channel 1120 has a first end open to the cavity 111A and a bottom open to a bottom of the shank 112. Threads 112E are formed on a peripheral surface of the channel 112D. An externally threaded member 50 has first threads 151 on a lower portion secured to the threads 112E, and second threads 152 on an upper portion secured to the threads 112E. The force transducer and transmitter assembly 140 is provided on an intermediate surface of the externally threaded member 50. The electrical resonant transformation device 200 and the solar controller and display device 300 are electrically connected by wire.

While the invention has been described in terms of preferred embodiments, those skilled in the art will recognize that the invention can be practiced with modifications within the spirit and scope of the appended claims.

What is claimed is:

1. A bolt tension gauging apparatus comprising:
   an electrical resonant transformation device;
   a controller and display device; and
   a bolt assembly comprising a bolt including a head having a cavity on a top, and a partially threaded shank having a recess on a peripheral surface, and a covering element configured to fit onto the recess; an electrical resonant transformer formed on a bottom of the covering member and configured to dispose in the cavity; and a force transducer and transmitter assembly disposed in the recess, the force transducer and transmitter assembly being electrically connected to the electrical resonant transformer;
   wherein the electrical resonant transformation device is configured to cause the electrical resonant transformer to harvest power from radio frequency electromagnetic waves transmitted from the electrical resonant transformation device if a distance between the electrical resonant transformation device and the electrical resonant transformer is no more than a predetermined distance;
   wherein the power is supplied from the electrical resonant transformer transformer to the force transducer and transmitter assembly for activation;
   wherein the activated force transducer and transmitter assembly gauges tension of the bolt and convert the gauged tension into a signal representing the gauged tension;
   wherein the signal is transmitted to the controller and display device so that the controller and display device calculates a difference between a predetermined tension and the gauged tension; and
   wherein an alert is generated if the gauged tension is greater than the predetermined tension.

2. The bolt tension gauging apparatus of claim 1, wherein the alert is audible.

3. The bolt tension gauging apparatus of claim 1, wherein the controller and display device includes a memory for storing the gauged tension.

4. The bolt tension gauging apparatus of claim 1, wherein the cavity communicates with the recess.

* * * * *